(12) United States Patent
Massey-Brooker et al.

(10) Patent No.: US 9,901,526 B2
(45) Date of Patent: Feb. 27, 2018

(54) CONSUMER GOODS PRODUCT COMPRISING FUNCTIONALISED LIGNIN OLIGOMER

(71) Applicant: The Procter & Gamble Company, Cincinnati, OH (US)

(72) Inventors: Anju Deepali Massey-Brooker, Newcastle upon Tyne (GB); Mauro Vaccaro, Newcastle upon Tyne (GB); Stefano Scialla, Strombeek-Bever (BE); Claudia Crestini, Rome (IT); Heiko Lange, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/189,019

(22) Filed: Jun. 22, 2016

(65) Prior Publication Data

US 2016/0374922 A1  Dec. 29, 2016

(30) Foreign Application Priority Data

Jun. 24, 2015 (EP) .................................... 15173603

(51) Int. Cl.

| | | |
|---|---|---|
| *C11D 3/37* | (2006.01) | |
| *A61K 8/72* | (2006.01) | |
| *A61Q 5/02* | (2006.01) | |
| *A61Q 5/12* | (2006.01) | |
| *A61Q 11/00* | (2006.01) | |
| *A61Q 19/00* | (2006.01) | |
| *C07G 1/00* | (2011.01) | |
| *C08H 7/00* | (2011.01) | |
| *C09G 1/00* | (2006.01) | |
| *C11D 3/382* | (2006.01) | |
| *C08L 97/00* | (2006.01) | |
| *A61K 8/29* | (2006.01) | |
| *A61K 8/31* | (2006.01) | |
| *A61K 8/34* | (2006.01) | |
| *A61K 8/368* | (2006.01) | |
| *A61K 8/37* | (2006.01) | |
| *A61K 8/41* | (2006.01) | |
| *A61K 8/42* | (2006.01) | |
| *A61K 8/44* | (2006.01) | |
| *A61K 8/49* | (2006.01) | |
| *A61K 8/60* | (2006.01) | |
| *A61K 8/63* | (2006.01) | |
| *A61K 8/64* | (2006.01) | |
| *A61K 8/81* | (2006.01) | |
| *A61K 8/898* | (2006.01) | |
| *A61K 47/30* | (2006.01) | |
| *C11D 17/06* | (2006.01) | |
| *C11D 3/386* | (2006.01) | |

(52) U.S. Cl.
CPC .................. *A61K 8/72* (2013.01); *A61K 8/29* (2013.01); *A61K 8/31* (2013.01); *A61K 8/34* (2013.01); *A61K 8/342* (2013.01); *A61K 8/345* (2013.01); *A61K 8/368* (2013.01); *A61K 8/37* (2013.01); *A61K 8/416* (2013.01); *A61K 8/42* (2013.01); *A61K 8/44* (2013.01); *A61K 8/498* (2013.01); *A61K 8/4926* (2013.01); *A61K 8/60* (2013.01); *A61K 8/63* (2013.01); *A61K 8/64* (2013.01); *A61K 8/8158* (2013.01); *A61K 8/898* (2013.01); *A61K 47/30* (2013.01); *A61Q 5/02* (2013.01); *A61Q 5/12* (2013.01); *A61Q 11/00* (2013.01); *A61Q 19/00* (2013.01); *C07G 1/00* (2013.01); *C08H 6/00* (2013.01); *C08L 97/005* (2013.01); *C09G 1/00* (2013.01); *C11D 3/3757* (2013.01); *C11D 3/382* (2013.01); *C11D 17/06* (2013.01); *A61K 2800/40* (2013.01); *C11D 3/38609* (2013.01); *C11D 3/38618* (2013.01); *C11D 3/38627* (2013.01)

(58) Field of Classification Search
None
See application file for complete search history.

(56) References Cited

U.S. PATENT DOCUMENTS

| | | | |
|---|---|---|---|
| 2,352,021 | A | 6/1944 | Schubert et al. |
| 3,912,706 | A | 10/1975 | Rachor et al. |
| 5,512,276 | A | 4/1996 | Lang et al. |
| 6,100,385 | A | 8/2000 | Naae et al. |
| 8,075,637 | B2 | 12/2011 | Gizaw et al. |
| 2003/0139319 | A1 | 7/2003 | Scheibel |
| 2003/0156970 | A1 | 8/2003 | Oberkofler et al. |
| 2008/0125544 | A1 | 5/2008 | Yao |
| 2010/0075878 | A1 | 3/2010 | Gizaw et al. |
| 2011/0114539 | A1 | 5/2011 | Stokes et al. |
| 2013/0233037 | A1 | 9/2013 | Adam |
| 2016/0374921 | A1 | 12/2016 | Massey-Brooker et al. |
| 2016/0374928 | A1 | 12/2016 | Massey-Brooker et al. |
| 2016/0374935 | A1 | 12/2016 | Massey-Brooker et al. |
| 2016/0375138 | A1 | 12/2016 | Massey-Brooker et al. |
| 2016/0376408 | A1 | 12/2016 | Massey-Brooker et al. |

FOREIGN PATENT DOCUMENTS

| | | |
|---|---|---|
| CN | 104 147 977 A | 11/2014 |
| JP | S63 97612 A | 4/1988 |

(Continued)

OTHER PUBLICATIONS

Lora, Jairo H., et al., Recent Industrial Applications of Lignin: A Sustainable Alternative to Nonrenewable Materials, Journal of Polymers and the Environment, Apr. 2002, pp. 39-48, vol. 10, Nos. 112, XP-002493248.

(Continued)

*Primary Examiner* — Brian Gulledge
(74) *Attorney, Agent, or Firm* — John T. Dipre; Steven W. Miller

(57) ABSTRACT

A consumer goods product comprising a consumer goods product ingredient and a cross-linked co-polymer of a lignin oligomer and a vinyl monomer, wherein the lignin oligomer has: (a) comprises less than 1 wt % sulphur content; (b) has a number average molecular weight ($\overline{M}_n$) of from 800 Da to 1,800 Da; and (c) has an average number of lignin monomers of from 3 to 8.

19 Claims, No Drawings

(56) References Cited

FOREIGN PATENT DOCUMENTS

| JP | H07 215988 A | 8/1995 |
| WO | WO 2010/135804 A1 | 12/2010 |
| WO | WO 2010/135805 A1 | 12/2010 |
| WO | WO 2014/178911 A1 | 11/2014 |

OTHER PUBLICATIONS

Pan, Xuejun, et al., Organosolv Ethanol Lignin from Hybrid Poplar as a Radical Scavenger: Relationship between Lignin Structure, Extraction Conditions, and Antioxidant Activity, J. Agric. Food Chem., 2006, pp. 5806-5813, vol. 54, XP008148495.

Ugartondo, Vanessa, et al., Comparative antioxidant and cytotoxic effects of lignins from different sources, Bioresource Technology, 2008, pp. 6683-6687, vol. 99.

Zhang, Jianfeng, et al., Reductive Degradation of Lignin and Model Compounds by Hydrosilanes, ACS Sustainable Chemistry & Engineering, 2014, pp. 1983-1991, vol. 2.

Uraki, Yasumitsu, et al., Novel Functions of Non-Ionic, Amphiphilic Lignin Derivatives In: ACS Symposium Series, Jan. 1, 2012, pp. 243-254, American Chemical Society/ Oxford University Press, vol. 1107, Chapter 13, XP055235971.

Extended European Search Report; Application No. 15173599.0-1460; dated Jan. 15, 2016, 9 pages.

Extended European Search Report; Application No. 15173603.0-1460; dated Jan. 15, 2016, 8 pages.

Database GNPD [Online], MINTEL, Mar. 2009, "Eye Contour Cream", XP002751692, Database accession No. 1102156, *the whole document*.

Database GNPD [Online], MINTEL, Apr. 2012, "Aloe Vera Shower Gel", XP002751693, Database accession No. 1765683, *the whole document*.

U.S. Appl. No. 15/189,005, filed Jun. 22, 2016, Massey-Brooker, et al.

U.S. Appl. No. 15/189,007, filed Jun. 22, 2016, Massey-Brooker, et al.

U.S. Appl. No. 15/189,009, filed Jun. 22, 2016, Massey-Brooker, et al.

U.S. Appl. No. 15/189,011, filed Jun. 22, 2016, Massey-Brooker, et al.

U.S. Appl. No. 15/189,016, filed Jun. 22, 2016, Massey-Brooker, et al.

CONSUMER GOODS PRODUCT COMPRISING FUNCTIONALISED LIGNIN OLIGOMER

FIELD OF THE INVENTION

The present invention relates to consumer goods products comprising functionalized liginin oligomer.

BACKGROUND OF THE INVENTION

Cross-linked co-polymers based vinyl monomers such as acrylic acid and/or methacrylic acid provide rheology modification benefits. However, the cross-linking agents commonly used to make these cross-linked co-polymers such as divinyl benzene are highly hydrophobic and not readily soluble in water. Therefore, the cross-linking increases the hydrophobicity of the final cross-linked co-polymer.

The use of lignin-oligomers as cross-linking agents for polymers based on vinyl monomers results in cross-linked co-polymers without the unwanted increase in hydrophobicity. These cross-linked co-polymers exhibit improved solubility.

SUMMARY OF THE INVENTION

A consumer goods product comprising a consumer goods product ingredient and a cross-linked co-polymer of a lignin oligomer and a vinyl monomer, wherein the lignin oligomer has: (a) comprises less than 1 wt % sulphur content; (b) has a number average molecular weight ($\overline{M}_n$) of from 800 Da to 1,800 Da; and (c) has an average number of lignin monomers of from 3 to 8.

DETAILED DESCRIPTION OF THE INVENTION

Consumer Goods Product:

A consumer goods product comprising a consumer goods product ingredient and a cross-linked co-polymer of a lignin oligomer and a vinyl monomer, wherein the lignin oligomer has: (a) comprises less than 1 wt % sulphur content; (b) has a number average molecular weight ($\overline{M}_n$) of from 800 Da to 1,800 Da; and (c) has an average number of lignin monomers of from 3 to 8.

The consumer goods product may comprise an emollient and/or humectant.

The consumer goods product may comprise an emulsifier, this may be preferred when the lignin oligomer is in the form of an emulsion.

The consumer goods product may be a skin treatment composition.

The consumer goods product may be a hair treatment composition.

The consumer goods product may be an oral care composition.

The consumer goods product may be an antiseptic cream.

The consumer goods product may be a shoe polish.

The consumer goods product may be a detergent composition.

The consumer goods product may comprise chitin and/or chitin derivatives.

The consumer goods product is typically selected from: feminine pad; diaper; razor blade strip; hard surface cleaning sheet and/or wipe; and teeth treatment strip.

The consumer goods product is typically selected from: skin cream; skin lotion; shaving preparation gel or foam; handwash laundry detergent; handwash dishwashing detergent; soap bar; liquid handwash soap; body wash; toothpaste; shampoo; and conditioner.

Consumer Goods Product Ingredient:

Suitable consumer goods product ingredients include emollient, humectants, emulsifiers, and any combination thereof.

Cross-Linked Co-Polymer:

The cross-linked co-polymer is a co-polymer of a lignin oligomer and a vinyl monomer.

The cross-linked co-polymer may comprise a structural motif selected from:

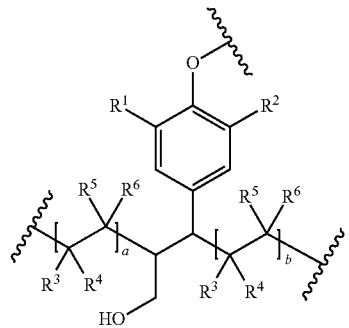

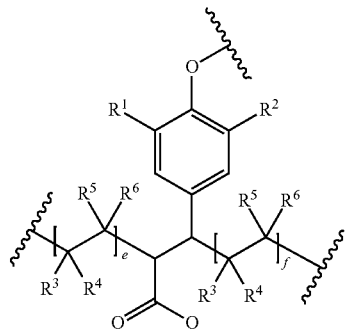

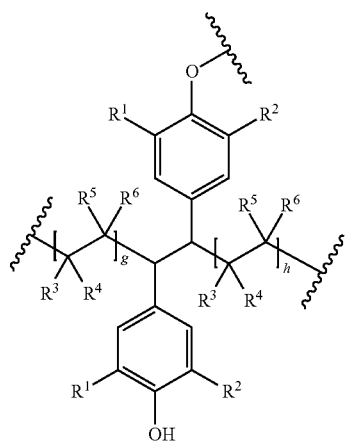

-continued

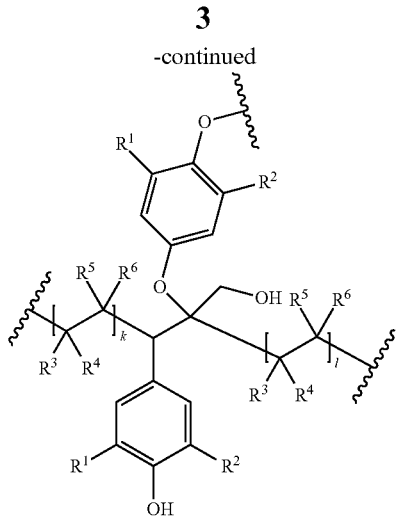

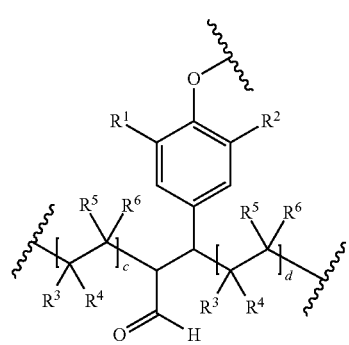

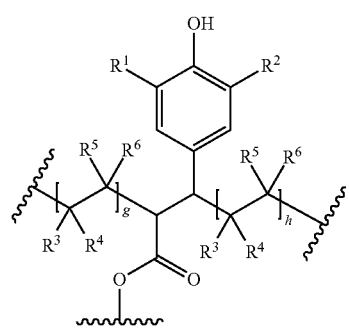

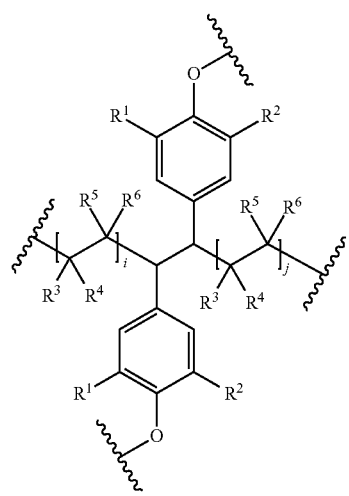

-continued

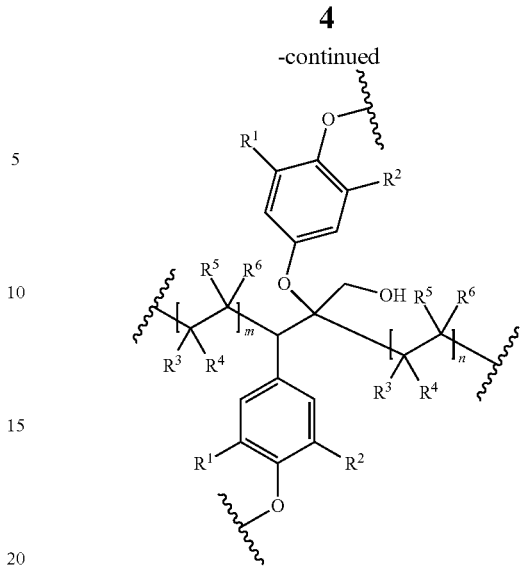

H-type: $R^1 = R^2 = H$
G-type: $R^1 = H, R^2 = OMe$
S-type: $R^1 = R^2 = OMe$

The cross-linked co-polymer comprises the structural motif:

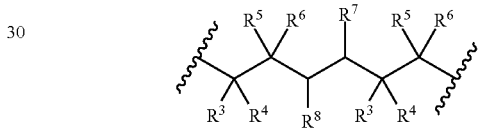

wherein $R^3$, $R^4$, $R^5$ and $R^6$ are independently selected from H, methyl, COOH, COOMe, pyrrolidinone, imidazole and imidazolium,
wherein, with the exception of H, no more than two of these groups can be linked to the same carbon atom,
wherein each carbon carries at least one H.
wherein $R^7$ and $R^8$ are representing the lignin backbone that are connected to the carbon-carbon double bond motif.

The carbon-carbon double bond motif is typically selected from stilbenes, aryl-enol ethers, cinnamyl alcohols, cinnamyl aldehydes, cinnamyle acids, and cinnamyl esters, any derivative thereof, and any combination thereof Lignin Oligomer:

The lignin oligomer has: (a) comprises less than 1 wt % sulphur content; (b) has a number average molecular weight ($\overline{M}_n$) of from 800 Da to 1,800 Da; and (c) has an average number of lignin monomers of from 3 to 8.

Preferably, the lignin oligomer has a hydroxyl content of from 3 mmol/g to 5.7 mmol/g.

Preferably, the lignin oligomer comprises less than 1 wt % sulphur content.

Preferably, the lignin oligomer has a molar ratio of aromatic hydroxyl content to aliphatic hydroxyl content in the range of from 1:1 to 1.5:1.

Preferably, the lignin oligomer has a weight average molecular weight ($\overline{M}_w$) in the range of from 800 Da to 5000 Da.

Preferably, the lignin oligomer has a number average molecular weight ($\overline{M}_n$) in the range of from 800 Da to 1200 Da.

Preferably, the lignin oligomer is essentially free of sulphur.

Preferably, the lignin oligomer has an ester content in the range of from 0.0 mmol/g to 0.1 mmol/g.

Preferably, the lignin oligomer is derived from corn, sugar cane, wheat and any combination thereof Preferably, the lignin oligomer is obtained by an organosolv-like isolation process for the lignins, using preferentially wheat straw, corn stover and/or sugar cane bagasse lignin starting materials.

Preferably, the ratio of aromatic hydroxyl groups to aliphatic hydroxyl groups of the lignin oligomer is within the range of 1.2 to 1.9.

Preferably, the lignin oligomer has a hydrolysable ester content in the range of from 0.2 to 0.5 mmol/g. The hydrolysable ester content preferably comprises acetate and formate functional groups.

Vinyl Monomer:

The vinyl monomer is typically selected from acrylic acid or acrylic acid esters, methacrylic acid or methacrylic acid esters, vinylpyrrolidone, vinylimidazole, vinylimidazolinium and any combination thereof.

The vinyl monomer may be selected from acrylic acid, methacrylic acid and any combination thereof.

Method of Measuring Sulphur Content:

The chemical composition of a lignin sample in terms of its carbon (C), hydrogen (H), nitrogen (N) and sulphur (S) content can be determined by elemental analysis in form of a CHNS analysis of at least three different representative samples of a given batch of the respective lignin. Typical sample sizes are 2.0 mg of a lignin sample that was oven-dried at 105° C. until a steady weight was obtained. The samples are placed in aluminum dishes and analyzed using a Carlo-Erba NA 1500 analyzer, using helium as carrier gas. Carbon (C), hydrogen (H), nitrogen (N) and sulphur (S) were detected in form of carbon dioxide, water, nitrogen, and sulphur dioxide, which are chromatographically separated to exit the instrument in the order of nitrogen, carbon dioxide, water, and sulphur dioxide. Quantification is achieved against calibrations using typical standard substances used for the calibration of elemental analysers, such as (bis(5-tert-butyl-2-benzo-oxazol-2-yl) thiophene, based on the peak areas of the chromatograms obtained for each lignin sample.

Method of Measuring $\overline{M}_n$ and $\overline{M}_w$:

The number average molecular weight, $\overline{M}_n$, as well as the weight average molecular weight, $\overline{M}_w$, can be determined using gel permeation chromatography (GPC). Prior to analysis, representative lignin samples are acetobrominated as reported in archival literature (J. Asikkala, T. Tamminen, D. S. Argyropoulos, J. Agric. Food Chem. 2012, 60, 8968-8973.) to ensure complete solubilisation in tetrahydrofuran (THF). 5 mg lignin is suspended in 1 mL glacial acetic acid/acetyl bromide (9:1 v/v) for 2 h. The solvent is then removed under reduced pressure, and the residue is dissolved in HPLC-grade THF and filtered over a 0.45 μm syringe filter prior to injection into a 20 μL sample loop. Typical analysis set-ups resemble the following specific example: GPC-analyses are performed using a Shimadzu instrument consisting of a controller unit (CBM-20A), a pumping unit (LC 20AT), a degasser unit (DGU-20A3), a column oven (CTO-20AC), a diode array detector (SPD-M20A), and a refractive index detector (RID-10A); the instrumental set-up is controlled using the Shimadzu LabSolution software package (Version 5.42 SP3). Three analytical GPC columns (each 7.5×30 mm) are connected in series for analyses: Agilent PLgel 5 μm 10000 Å, followed by Agilent PLgel 5 μm 1000 Å and Agilent PLgel 5 μm 500 Å. HPLC-grade THF (Chromasolv®, Sigma-Aldrich) is used as eluent (isocratic at 0.75 mL min$^{-1}$, at 40° C.). Standard calibration is performed with polystyrene standards (Sigma Aldrich, MW range 162-5×106 g mol$^{-1}$), and lower calibration limits are verified/adjusted by the use of synthesized dimeric and trimeric lignin models. Final analyses of each sample is performed using the intensities of the UV signal at λ=280 nm employing a tailor-made MS Excel-based table calculation, in which the number average molecular weight ($\overline{M}_n$) and the weight average molecular weight ($\overline{M}_w$)) is calculated based on the measured absorption (in a.u.) at a given time (min) after corrections for baseline drift and THF-stemming artifacts.

$\overline{M}_n$ is calculated according to the formula $$\overline{M}_n = \frac{\sum w_i}{\sum \frac{w_i}{M_i}}$$

in which $\overline{M}_n$ is the number average molecular weight
$w_i$ is obtained via $$w_i = -h_i \frac{dV}{d(\log M)}$$

with M being molecular weight
hi being the signal intensity of a given log M measurement point
V being the volume of the curve over a given log M interval d(log M).
$M_i$ is a given molecular weight.
The analysis is run in triplicate, and final values are obtained as the standard average.

$\overline{M}_w$ is calculated according to the formula $$\overline{M}_w = \frac{\sum w_i M_i}{\sum w_i}$$

in which $\overline{M}_w$ is the number average molecular weight
$w_i$ is obtained via $$w_i = -h_i \frac{dV}{d(\log M)}$$

with M being the molecular weight
hi being the signal intensity of a given log M measurement point
V being the volume of the curve over a given log M interval d(log M).
$M_i$ is a given molecular weight.
The analysis is run in triplicate, and final values are obtained as the standard average.

Eventually necessary adjustment of $\overline{M}_n$ and $\overline{M}_w$ with respect to the desired applications is achieved by mechanical breaking of polymeric lignin using a ball mill, by chemically or enzymatically polymerising oligomeric lignin.

Method of Measuring Aromatic Hydroxyl and Aliphatic Hydroxyl Content:

Typically, a procedure similar to the one originally published can be used (A. Granata, D. S. Argyropoulos, J. Agric. Food Chem. 1995, 43, 1538-1544). A solvent mixture of pyridine and (CDCl3) (1.6:1 v/v) is prepared under anhydrous conditions. The NMR solvent mixture is stored over molecular sieves (4 Å) under an argon atmosphere. Cholesterol is used as internal standard at a concentration of 0.1 mol/L in the aforementioned NMR solvent mixture. 50 mg of Cr(III) acetyl acetonate are added as relaxation agent to this standard solution.

Ca. 30 mg of the lignin are accurately weighed in a volumetric flask and suspended in 400 µL of the above prepared solvent solution. One hundred microliters of the internal standard solution are added, followed by 100 µL of 2-chloro-4,4,5,5-tetramethyl-1,3,2-dioxaphospholane (Cl-TMDP). The flask is tightly closed, and the mixture is stirred for 120 min at ambient temperature. 31P NMR spectra are recorded using suitable equipment, similar or identical to the following example: On a Bruker 300 MHz NMR spectrometer, the probe temperature is set to 20° C. To eliminate NOE effects, the inverse gated decoupling technique is used. Typical spectral parameters for quantitative studies are as follows: 90° pulse width and sweep width of 6600 Hz. The spectra are accumulated with a delay of 15 s between successive pulses. Line broadening of 4 Hz is applied, and a drift correction is performed prior to Fourier transform. Chemical shifts are expressed in parts per million from 85% H3PO4 as an external reference. All chemical shifts reported are relative to the reaction product of water with Cl-TMDP, which has been observed to give a sharp signal in pyridine/CDCl3 at 132.2 ppm. To obtain a good resolution of the spectra, a total of 256 scans are acquired. The maximum standard deviation of the reported data is 0.02 mmol/g, while the maximum standard error is 0.01 mmol/g. (A. Granata, D. S. Argyropoulos, J. Agric. Food Chem. 1995, 43, 1538-1544). Quantification on the basis of the signal areas at the characteristic shift regions (in ppm, as reported in A. Granata, D. S. Argyropoulos, J. Agric. Food Chem. 1995, 43, 1538-1544) is done using a tailor-made table calculation in which the abundances, given in mmol/g, of the different delineable phosphitylated hydroxyl groups are determined on the basis of the integral obtained for the signal of the internal standard, that is present in the analysis sample at a concentration of 0.1 m, creating a signal at the interval ranging from 144.5 ppm to 145.3 ppm. The area underneath the peak related to the internal standard is set to a value of 1.0 during peak integration within the standard processing of the crude NMR data, allowing for determining abundances using simple rule-of-proportion mathematics under consideration of the accurate weight of the sample used for this analysis. The analysis is run in triplicate, and final values are obtained as the standard average.

Method of Measuring Hydrolysable Ester Content:

The total ester content of the lignin can be determined by subjecting the lignin to alkaline hydrolysis conditions: Ca. 500 mg of lignin are dissolved in an excess of 1 M sodium hydroxide solution and heated to temperatures of above 70-80° C. for 12 h. The lignin is subsequently precipitated by acidifying the reaction mixture, isolated and freeze-dried.

Ca. 30 mg of the lignin are accurately weighed in a volumetric flask and suspended in 400 µL of the above prepared solvent solution. One hundred microliters of the internal standard solution are added, followed by 100 µL of 2-chloro-4,4,5,5-tetramethyl-1,3,2-dioxaphospholane (Cl-TMDP). The flask is tightly closed, and the mixture is stirred for 120 min at ambient temperature. $^{31}$P NMR spectra are recorded using suitable equipment under the conditions reported above for the determination of aliphatic and aromatic hydroxyl contents. Quantification of the acid content is done on the basis of the signal intensities at the characteristic shift regions (in ppm) using a tailor-made table calculation referring to the signal of the internal standard. Abundances are typically given in mmol/g. The ester content is obtained as the difference in the abundances of acid groups, aliphatic hydroxyl groups, and aromatic hydroxyl groups found in untreated vs. the lignin treated with sodium hydroxide as outlined above. The analysis is run in triplicate, and final values are obtained as the standard average.

Method of Measuring Double Bond Content of Starting Lignins:

Lignin oligomers are acetylated in pyridine/acetic anhydride (V/V=1:1) at 50° C. for 48 h. Ethanol was added, and the volatiles were removed in vacuo; the procedure was repeated twice. Then, toluene was added, and the volatiles were quickly removed in vacuo, this was repeated twice, as well. Finally, chloroform was added, and the volatiles were removed in vacuo; again, this was repeated twice. The solid was then dried overnight in vacuo.

Measurements: All spectra were acquired at 303 K with a Bruker Avance 600 spectrometer equipped with a cryoprobe. The sample consisted of 80 mg of acetylated lignin dissolved in 600 µL of deuterated dimethylsulfoxide (DMSO-$d_6$). A matrix consisting of 400×2048 points was obtained in eight scans. Either QQ-HSQC measurements or HSQC$_0$ measurements are performed. QQ-HSQC measurements were performed in accordance with the original reference [D. J. Peterson, N. M. Loening, Magn. Reson. Chem. 2007, 45, 937-941.] as reported before [C. Crestini, F. Melone, M. Sette, R. Saladino, Biomacromolecules 2011, 12, 3928-3935; M. Sette, R. Wechselberger, C. Crestini, Chem. Eur. J. 2011, 17, 9529-9535]. In the HSQC$_0$-related measurements, the second and third HSQC were obtained as repetitions of the basic HSQC scheme, according to the published procedure [K. Hu, W. M. Westler, J. L. Markley, J. Am. Chem. Soc. 2011, 133, 1662-1665; M. Sette, H. Lange, C. Crestini, Comput. Struct. Biotechnol. J. 2013, 6, e201303016].

Data processing: NMR data were processed with MestreNova (Version 8.1.1, Mestrelab Research) by using a 60°-shifted square sine-bell apodisation window; after Fourier transformation and phase correction a baseline correction was applied in both dimensions. The final matrix consisted of 1024×1024 points, and cross-peaks were integrated with the same software that allows the typical shape of peaks present in the spectrum to be taken into account. Extrapolations based on the values of the volumes of the peaks of interest of the three consecutive HSQC measurements were performed using MS Excel 2010, to yield the volumes of the different peaks for quantitative analyses.

Double bond containing structural units apart from aromatic structures in the lignin backbone are expressed in a generic double bond-equivalent for a given lignin.

How to Functionalise the Starting Lignin with Vinylic Reactants:

In the following, the term 'lignin' refers to all lignins covered by the definitions outlined in this document.

In the following, the term 'vinylic reactants' stands exemplary for all monomeric, oligomeric and polymeric molecules that i) exhibit at least one double bond equivalent in their structure, and that ii) were, in any case apart from monomeric substances, obtained by polymerisation of double bond-containing monomers.

In the following, radical starters can also be enzymes, recruited preferentially but not exclusively from the classes of laccases and lipoxygenases.

In the following, solvents can be organic solvents or aqueous solutions containing salts necessary for creating suitable environments for enzymes.

Depending on the choice of radical starter, and depending on the degree of control that is desired in the radical polymerisation reactions underlying the functionalisation of lignin with vinylic reactants, the temperatures for the reactions are chosen.

Example Reaction:

In a typical set-up, acrylic acid (x mg) is mixed with wheat straw biolignin (y mg), in 10 mL of toluene. Azobisisobutyronitril (AIBN) (100 mg) is added as radical starter and the reaction is stirred at 80° C. Once the reaction is finished after 12 h, the solvent is removed under reduced pressure to yield the newly formed lignin-vinyl species co-polymer. In case of enzymatically triggered reactions, enzymes and buffer salts are separated from the newly formed lignin-vinyl species hybrid by a suitable form of washing or dialysis.

How to Characterise and Quantify Functionalisation Content:

In the following, the term 'lignin' refers to all lignins covered by the definitions outlined in this document.

In the following, the term 'vinylic reactants' stands exemplary for all monomeric, oligomeric and polymeric molecules that i) exhibit at least one double bond equivalent in their structure, and that ii) were, in any case apart from monomeric substances, obtained by polymerisation of double bond-containing monomers.

Evaluation of Bonding Type:

Bonds between lignin starting materials and vinylic reactants are preferentially but eventually not exclusively formed between the double bond equivalent of the lignin substrate and the double bonds in the vinylic reactants. Bonding patterns and preferred bonding sites are determined and quantitatively estimated via quantitative two-dimensional NMR spectroscopy in form of quantitative HSQC measurements on the novel lignin-vinyl species hybrids after permethylating them using diazomethane as methylating reagent under standard textbook conditions. Quantitative HSQCs were obtained according to above mentioned experimental specifications in form of QQ-HSQC measurements or $HSQC_0$ measurements.

Quantification of Vinylic Reactant in Novel Lignin-Vinyl Species Hybrids:

Novel lignin-vinyl species hybrids are permethylated using diazomethane as methylating reagent under standard textbook conditions. ca. 50 mg of permethylated hybrids are weighted exactly and dissolved in 600 μL deuterated dimethylsulfoxide (DMSO-$d_6$), mixed with 2 mg of chromium acetylacetonate and an exact amount of ca. 3 mg of trioxane as internal standard. This mixture is subjected to quantitative $^{13}C$ NMR spectroscopy. Quantification is based on the relative intensities of the signals stemming from carbon atoms in the lignin backbone and the grafted vinyl reactants with respect to the internal standard trioxane. Functional group contents are expressed in the lignin content of the novel hybrid material in % (m/m) lignin.

Emollient:

Suitable emollients are silicon based emollients. Silicone-based emollients are organo-silicone based polymers with repeating siloxane (Si 0) units. Silicone-based emollients of the present invention are hydrophobic and exist in a wide range of molecular weights. They include linear, cyclic and crosslinked varieties. Silicone oils are generally chemically inert and usually have a high flash point. Due to their low surface tension, silicone oils are easily spreadable and have high surface activity. Examples of silicon oil include: Cyclomethicones, Dimethicones, Phenyl-modified silicones, Alkyl-modified silicones, Silicones resins, Silica.

Other emollients useful in the present invention can be unsaturated esters or fatty esters. Examples of unsaturated esters or fatty esters of the present invention include: Caprylic Capric Triglycerides in combination with Bis-PEG/PPG-1 6/16 PEG/PPG-16/16 Dimethicone and C12-C15 Alkylbenzoate.

The basic reference of the evaluation of surface tension, polarity, viscosity and spreadability of emollient can be found under Dietz, T., Basic properties of cosmetic oils and their relevance to emulsion preparations. SOFW-Journal, July 1999, pages 1-7.

Humectant:

A humectant is a hygroscopic substance used to keep things moist. Typically, it is often a molecule with several hydrophilic groups, most often hydroxyl groups; however, amines and carboxyl groups, sometimes esterified, can be encountered as well (its affinity to form hydrogen bonds with molecules of water is the crucial trait). A humectant typically attracts and retains the moisture in the air nearby via absorption, drawing the water vapour into and/or beneath the organism/object's surface.

Suitable humectants include: Propylene glycol, hexylene glycol, and butylene glycol, Glyceryl triacetate, Neoagarobiose, Sugar alcohols (sugar polyols) such as glycerol, sorbitol, xylitol, maltitol, Polymeric polyols such as polydextrose, *Quillaia*, Urea, Aloe vera gel, MP diol, Alpha hydroxy acids such as lactic acid, Honey, Lithium chloride Emulsifier:

An emulsifier generally helps disperse and suspend a discontinuous phase within a continuous phase in an oil-in-water emulsion. A wide variety of conventional emulsifiers are suitable for use herein. Suitable emulsifiers include: hydrophobically-modified cross-linked polyacrylate polymers and copolymers, polyacrylamide polymers and copolymers, and polyacryloyldimethyl taurates. More preferred examples of the emulsifiers include: acrylates/C10-30 alkyl acrylate cross-polymer having tradenames Pemulen™ TR-1, Pemulen™ TR-2 (all available from Lubrizol); acrylates/steareth-20 methacrylate copolymer with tradename ACRYSOL™ 22 (from Rohm and Hass); polyacrylamide with tradename SEPIGEL 305 (from Seppic).

EXAMPLES

Example 1

The following samples were evaluated by the method described below. Sample A is lignin oligomer cross-linked with vinyl acrylic acid co-polymer, Sample B comprises the lignin starting material and the starting unreactive vinylacrylic acid copolymer (comparative example). Sample is the invention examples and Sample B is the comparison example.

Preparation of Turbidity Samples:

Weigh out 0.1 g of lignin and dispersed of non-ionic based hard surface cleaning product water dispersion (Flash diluted in de-ionized water at the recommended dosage of 4.8 ml/l) and stir it for 15 minutes at 200 rpm at room temperature. Then, measure the turbidity of the aqueous dispersion using the above method with Turbiscan Ageing Station.

Turbidity Data:

| Sample name | % Transmission |
| --- | --- |
| Sample A | 28.00 |
| Sample B | 20.00 |

Sample A in accordance with the present invention showed higher transmission values corresponding to superior solubility properties than the comparison example (Sample B).

Example 2

Illustrative Examples

Shampoo Compositions:

| Ingredient | Wt. % Product I | Wt. % Product II |
| --- | --- | --- |
| Water | Balance | Balance |
| Cetyl Alcohol | 4.18% | 4.18% |
| Stearyl Alcohol | 7.52% | 7.52% |
| Sodium laureth-3 sulfate (28% Active) | 10.00% | 10.00% |
| Cross-linked co-polymer of a lignin oligomer and a vinyl monomer | 0.01% | 1.00% |

Hair Conditioning:

| Components | Wt % New Product I | Wt % New Product II |
| --- | --- | --- |
| Behenyl trimethylammonium methosulfate | 2.97 | — |
| Stearamidopropyl dimethyl amine | — | 3.24 |
| Dicetyl dimethyl ammonium chloride | — | — |
| Cetyl alcohol | 1.01 | 4.25 |
| Stearyl alcohol | 2.53 | 2.93 |
| Benzyl alcohol | 0.4 | 0.4 |
| Deionized Water | Balance | Balance |
| L-glutamic acid | — | 1.04 |
| Preservative (Kathon CG) | 0 | 0 |
| Cross-linked co-polymer of a lignin oligomer and a vinyl monomer | 0.01 | 1.00 |
| Aminosilicone *3 | 1.5 | 1.5 |
| Perfume | 0.5 | 0.5 |

Hand Dishwashing:

| Examples | Wt % Product I | Wt % Product II |
| --- | --- | --- |
| Alkyl ethoxy sulfate AExS | 16 | 16 |
| Amine oxide | 5.0 | 5.0 |
| C9-11 EO8 | 5 | 5 |
| GLDA | 0.7 | 0.7 |
| Solvent | 1.3 | 1.3 |
| Polypropylene glycol (Mn = 2000) | 0.5 | 0.5 |
| Sodium chloride | 0.8 | 0.8 |
| Cross-linked co-polymer of a lignin oligomer and a vinyl monomer | 0.01 | 1.0 |
| Water | Balance | Balance |

Granular Laundry Detergent Compositions Designed for Front-Loading Automatic Washing Machines:

| | Wt % Product I | Wt % Product II |
| --- | --- | --- |
| Linear alkylbenzenesulfonate | 8 | 8 |
| C12-14 Alkylsulfate | 1 | 1 |
| AE7 | 2.2 | 2.2 |
| $C_{10-12}$ Dimethyl hydroxyethylammonium chloride | 0.75 | 0.75 |
| Crystalline layered silicate ($\delta$-$Na_2Si_2O_5$) | 4.1 | 4.1 |
| Zeolite A | 5 | 5 |
| Citric Acid | 3 | 3 |
| Sodium Carbonate | 15 | 15 |
| Silicate 2R ($SiO_2:Na_2O$ at ratio 2:1) | 0.08 | 0.08 |
| Soil release agent | 0.75 | 0.75 |
| Acrylic Acid/Maleic Acid Copolymer | 1.1 | 1.1 |
| Carboxymethylcellulose | 0.15 | 0.15 |
| Protease - Purafect ® (84 mg active/g) | 0.2 | 0.2 |
| Amylase - Stainzyme Plus ® (20 mg active/g) | 0.2 | 0.2 |
| Lipase - Lipex ® (18.00 mg active/g) | 0.05 | 0.05 |
| Amylase - Natalase ® (8.65 mg active/g) | 0.1 | 0.1 |
| TAED | 3.6 | 3.6 |
| Percarbonate | 13 | 13 |
| Na salt of Ethylenediamine-N,N'-disuccinic acid, (S,S) isomer (EDDS) | 0.2 | 0.2 |
| Hydroxyethane di phosphonate (HEDP) | 0.2 | 0.2 |
| $MgSO_4$ | 0.42 | 0.42 |
| Perfume | 0.5 | 0.5 |
| Suds suppressor agglomerate | 0.05 | 0.05 |
| Soap | 0.45 | 0.45 |
| Sulphonated zinc phthalocyanine (active) | 0.0007 | 0.0007 |
| S-ACMC | 0.01 | 0.01 |
| Cross-linked co-polymer of a lignin oligomer and a vinyl monomer | 0.01 | 1.0 |
| Sulfate/Water & Miscellaneous | Balance | Balance |

Beauty Lotion/Cream:

| | Wt % Product I | Wt % Product II |
| --- | --- | --- |
| Water | Balance | Balance |
| Glycerin | 7 | 7 |
| Disodium EDTA | 0.05 | 0.05 |
| Methylparaben | 0.1 | 0.1 |
| Sodium Dehydroacetate | 0.5 | 0.5 |
| Benzyl alcohol | 0.25 | 0.25 |
| GLW75CAP-MP (75% aq. TiO2 dispersion)[1] | 0.5 | 0.5 |
| Palmitoyl-dipeptide[2] | 0.0001 | 0.0001 |
| N-acetyl glucosamine | 2 | 2 |
| Salicylic Acid | 1.5 | 1.5 |
| Isohexadecane | 3 | 3 |
| PPG15 Steary1 Ether | 4 | 4 |
| Isopropyl Isostearate | 1.3 | 1.3 |
| Sucrose polyester | 0.7 | 0.7 |
| Phytosterol | 0.5 | 0.5 |
| Cetyl alcohol | 0.4 | 0.4 |
| Stearyl alcohol | 0.5 | 0.5 |
| Behenyl alcohol | 0.4 | 0.4 |
| PEG-100 stearate | 0.1 | 0.1 |
| Cetearyl glucoside | 0.1 | 0.1 |
| Polyacrylamide/C13-14 isoparaffin/laureth-7 | 2 | 2 |
| Dimethicone/dimethiconol | 2 | 2 |
| Polymethylsilsequioxane | 0.25 | 0.25 |
| Cross-linked co-polymer of a lignin oligomer and a vinyl monomer | 0.01 | 1.00 |

Personal Care Product Containing Skin Lightening:

| Component | Wt % Product I | Wt % Product II |
|---|---|---|
| Disodium EDTA | 0.100 | 0.100 |
| Phlorogine BG | 2.000 | 0 |
| deoxyArbutin | 0 | 2.000 |
| Niacinamide | 5.000 | 5.000 |
| Isohexadecane | 3.000 | 3.000 |
| Isopropyl isostearate | 1.330 | 1.330 |
| Sucrose polycottonseedate | 0.670 | 0.670 |
| Polymethylsilsesquioxane | 0.250 | 0.250 |
| Cetearyl glucoside + cetearyl alcohol | 0.200 | 0.200 |
| Behenyl alcohol | 0.400 | 0.400 |
| Ethylparaben | 0.200 | 0.200 |
| Propylparaben | 0.100 | 0.100 |
| Cetyl alcohol | 0.320 | 0.320 |
| Stearyl alcohol | 0.480 | 0.480 |
| Tocopheryl acetate | 0.500 | 0.500 |
| PEG-100 stearate | 0.100 | 0.100 |
| Glycerin | 7.000 | 7.000 |
| Titanium dioxide | 0.604 | 0.604 |
| Polyacrylamide + C13-14 isoparaffin + laureth-7 | 2.000 | 2.000 |
| Panthenol | 1.000 | 1.000 |
| Benzyl alcohol | 0.400 | 0.400 |
| Dimethicone + dimethiconol | 2.000 | 2.000 |
| Cross-linked co-polymer of a lignin oligomer and a vinyl monomer | 0.010 | 1.000 |
| Water (to 100 g) | Balance | Balance |

Automatic Dishwashing Cleaning Composition:

| | Powder (wt % based on 19 g portion) | Powder (wt % based on 19 g portion) |
|---|---|---|
| STPP | 34-38 | 34-38 |
| Alcosperse[1] | 7-12 | 7-12 |
| SLF-18 Polytergent[2] | 1-2 | 1-2 |
| Esterified substituted benzene sulfonate[3] | 0.1-6.0 | 0.1-6.0 |
| Polymer[4] | 0.2-6.0 | 0.2-6.0 |
| Sodium perborate monohydrate | 2-6 | 2-6 |
| Carbonate | 20-30 | 20-30 |
| 2.0r silicate | 5-9 | 5-9 |
| Sodium disilicate | 0-3 | 0-3 |
| Enzyme system[5] | 0.1-5.0 | 0.1-5.0 |
| Pentaamine cobalt(III)chloride dichloride salt | 10-15 | 10-15 |
| TAED | 0-3 | 0-3 |
| Perfume, dyes, water and other components | Balance to 100% | Balance to 100% |
| | Liquid (wt % based on 1.9 g portion) | Liquid (wt % based on 1.9 g portion) |
| Dipropylene Glycol | 35-45 | 35-45 |
| SLF-19 Polytergent[2] | 40-50 | 40-50 |
| Neodol ® C11EO9 | 1-3 | 1-3 |
| Cross-linked co-polymer of a lignin oligomer and a vinyl monomer | 0.01 | 1.0 |
| Dyes, water and other components | Balance | Balance |

[1] such as Alcosperse ® 246 or 247, a sulfonated copolymer of acrylic acid from Alco Chemical Co.
[2] linear alcohol ethoxylate from Olin Corporation
[3] such as those described above
[4] a sulfonated polymer such as those described above
[5] one or more enzymes such as protease, mannaway, natalase, lipase and mixture thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer goods product comprising a consumer goods product ingredient and a cross-linked co-polymer of a lignin oligomer and a vinyl monomer, wherein the lignin oligomer has:
   (a) comprises less than 1 wt % sulphur content;
   (b) has a number average molecular weight ($\overline{M}_n$) of from 800 Da to 1,800 Da; and
   (c) has an average number of lignin monomers of from 3 to 8.

2. A consumer goods product according to claim 1, wherein the vinyl monomer is selected from acrylic acid or acrylic acid esters, methacrylic acid or methacrylic acid esters, vinylpyrrolidone, vinylimidazole, vinylimidazolinium and any combination thereof.

3. A consumer consumer goods product according to claim 1, wherein the cross-linked co-polymer comprises the structural motif:

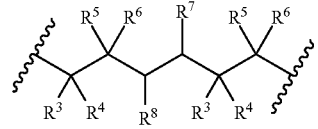

wherein $R^3$, $R^4$, $R^5$ and $R^6$ are independently selected from H, methyl, COOH, COOMe, pyrrolidinone, imidazole and imidazolium,
wherein, with the exception of H, no more than two of these groups can be linked to the same carbon atom,
wherein each carbon carries at least one H,
wherein $R^7$ and $R^8$ are representing the lignin backbone that are connected to the carbon-carbon double bond motif.

4. A consumer consumer goods product according to claim 3, wherein the carbon-carbon double bond motif is selected from stilbenes, aryl-enol ethers, cinnamyl alcohols, cinnamyl aldehydes, cinnamyle acids, and cinnamyl esters, any derivative thereof, and any combination thereof.

5. A consumer goods product according to claim 1, wherein the vinyl monomer is selected from acrylic acid, methacrylic acid and any combination thereof.

6. A consumer goods product according to claim 1, wherein the lignin oligomer is an unfunctionalised lignin oligomer.

7. A consumer goods product according to claim 1, wherein the lignin oligomer has a molar ratio of aromatic hydroxyl content to aliphatic hydroxyl content in the range of from 1:1 to 1.5:1.

8. A consumer goods product according to claim 1, wherein the lignin oligomer has a weight average molecular weight ($\overline{M}_w$) in the range of from 800 Da to 5000 Da.

9. A consumer goods product according to claim 1, wherein the lignin oligomer is essentially free of sulphur.

10. A consumer goods product according to claim 1, wherein the lignin oligomer has an ester content in the range of from 0.0 mmol/g to 0.1 mmol/g.

11. A consumer goods product according to claim 1, wherein the lignin oligomer is derived from corn, sugar cane, wheat and any combination thereof.

12. A consumer goods product according to claim 1, wherein the consumer goods product comprises an emollient and/or humectant.

13. A consumer goods product according to claim 1, wherein the consumer goods product comprises an emulsifier, and wherein the lignin oligomer is in the form of an emulsion.

14. A consumer goods product according to claim 1, wherein the product is a skin treatment composition.

15. A consumer goods product according to claim 1, wherein the product is a hair treatment composition.

16. A consumer goods product according to claim 1, wherein the product is an oral care composition.

17. A consumer goods product according to claim 1, wherein the product is an antiseptic cream.

18. A consumer goods product according to claim 1, wherein the product is a detergent composition.

19. A consumer goods product according to claim 1, wherein the consumer goods product comprises chitin and/or chitin derivatives.

* * * * *